United States Patent
Xu et al.

(10) Patent No.: US 10,772,932 B2
(45) Date of Patent: *Sep. 15, 2020

(54) MEDICAMENT FOR USE IN TREATING CARDIOVASCULAR AND CEREBROVASCULAR DISEASES

(71) Applicant: Shandong Zhonghai Pharmaceutical CO. LTD, Weifang (CN)

(72) Inventors: Baozhen Xu, Weifang (CN); Qian Cheng, Weifang (CN); Long Cheng, Weifang (CN)

(73) Assignee: SHANDONG ZHONGHAI PHARMACEUTICAL CO. LTD, Weifang (CN)

(*) Notice: Subject to any disclaimer, the term of this patent is extended or adjusted under 35 U.S.C. 154(b) by 0 days.

This patent is subject to a terminal disclaimer.

(21) Appl. No.: 16/073,867

(22) PCT Filed: Jan. 20, 2017

(86) PCT No.: PCT/CN2017/071851
§ 371 (c)(1),
(2) Date: Jul. 30, 2018

(87) PCT Pub. No.: WO2017/129056
PCT Pub. Date: Aug. 3, 2017

(65) Prior Publication Data
US 2019/0038709 A1    Feb. 7, 2019

(30) Foreign Application Priority Data

Jan. 29, 2016   (CN) .......................... 2016 1 0061770

(51) Int. Cl.
| | | |
|---|---|---|
| A61K 36/02 | (2006.01) | |
| A61K 31/715 | (2006.01) | |
| A61P 9/00 | (2006.01) | |
| A61P 3/06 | (2006.01) | |
| A61P 9/10 | (2006.01) | |
| A61P 9/12 | (2006.01) | |
| A61K 38/16 | (2006.01) | |
| A61K 36/315 | (2006.01) | |
| A61K 45/06 | (2006.01) | |
| A61K 38/02 | (2006.01) | |
| A61K 31/4025 | (2006.01) | |
| A61K 31/7012 | (2006.01) | |
| A61K 36/03 | (2006.01) | |
| A61K 36/04 | (2006.01) | |
| A61K 36/05 | (2006.01) | |
| A61K 36/48 | (2006.01) | |
| A61K 36/748 | (2006.01) | |

(52) U.S. Cl.
CPC ........ *A61K 38/168* (2013.01); *A61K 31/4025* (2013.01); *A61K 31/7012* (2013.01); *A61K 31/715* (2013.01); *A61K 36/02* (2013.01); *A61K 36/03* (2013.01); *A61K 36/04* (2013.01); *A61K 36/05* (2013.01); *A61K 36/315* (2013.01); *A61K 36/48* (2013.01); *A61K 36/748* (2013.01); *A61K 38/02* (2013.01); *A61K 45/06* (2013.01); *A61P 9/00* (2018.01)

(58) Field of Classification Search
None
See application file for complete search history.

(56) References Cited

U.S. PATENT DOCUMENTS

2010/0034757 A1*   2/2010   Fujii ..................... A61K 8/97
424/58

FOREIGN PATENT DOCUMENTS

| CN | 1260201 A | 7/2000 |
|---|---|---|
| CN | 1762341 A | 4/2006 |
| CN | 1844259 A | 10/2006 |
| CN | 1985847 A | 6/2007 |
| CN | 101357178 | * 2/2009 |
| CN | 101357178 A | 2/2009 |
| CN | 101481393 | * 7/2009 |
| CN | 101481393 A | 7/2009 |
| CN | 101760492 | * 6/2010 |
| CN | 101760492 A | 6/2010 |
| CN | 103393753 A | 11/2013 |
| CN | 103405685 | * 11/2013 |
| CN | 105617355 A | 6/2016 |

OTHER PUBLICATIONS

Altay et al. "Cerebrovascular inflammation after brief episodic hypoxia: modulation by neuronal and endothelial nitric oxide" J Apply Physiol 96, 1223-1230, 2004 (Year: 2004).*

* cited by examiner

*Primary Examiner* — Blaine Lankford
*Assistant Examiner* — Lauren K Van Buren
(74) *Attorney, Agent, or Firm* — Bayramogly Law Offices LLC

(57) ABSTRACT

A medicament for use in treating cardiovascular and cerebrovascular diseases, the medicament includes a marine algal glycoprotein.

1 Claim, No Drawings

MEDICAMENT FOR USE IN TREATING CARDIOVASCULAR AND CEREBROVASCULAR DISEASES

CROSS REFERENCE TO RELATED APPLICATIONS

This application is the national phase entry of International Application No. PCT/CN2017/071851, filed on Jan. 20, 2017, which is based upon and claims priority to Chinese Patent Application No. 201610061770.6, filed on Jan. 29, 2016, the entire contents of which are incorporated herein by reference.

TECHNICAL FIELD

The present invention relates to a medicament for use in treating cardiovascular and cerebrovascular diseases, and belongs to the technical field of medical technology.

BACKGROUND

Cardiovascular and cerebrovascular disease is a general term for diseases occurring in heart blood vessels and brain blood vessels, and are generally referred to as ischemic or hemorrhagic disease in heart, brain and systemic tissues caused by hyperlipidemia, blood viscosity, atherosclerosis, hypertension, etc. It is a common disease that seriously threatens the health of human beings, especially middle-aged and senile people aged above 50 years old. Even with the most advanced and improved treatment methods, more than 50% of survivors of cerebrovascular accidents cannot live completely on their own. The number of people that die from cardiovascular and cerebrovascular diseases every year all over the world is as high as 15 million, ranking first among all causes of death.

At present, the majority of medicaments commercially available for treating cardiovascular and cerebrovascular diseases are western medicines, they are compromised by certain deficiencies, such as proneness to generate medicament resistance. Although it is an anti-arrhythmic treating medicament, it can also cause arrhythmia itself, and these drugs have serious toxicity.

Patent: a traditional Chinese medicine composition for treating cardiovascular and cerebrovascular diseases, patent number is CN201310297384.3, it is disclosed that: a traditional Chinese medicine composition for treating cardiovascular and cerebrovascular diseases, which belonging to the technical field of Chinese herbal medicine preparations, and the technical problem to be solved is to provide a kind of an easy-to-carry and easy-to-take traditional Chinese medicine composition for treating cardiovascular and cerebrovascular diseases; the technical solution adopted is: a traditional Chinese medicine composition for treating cardiovascular and cerebrovascular diseases, comprising the following raw materials listed according to weight portions: 0.04-0.07 g of calculus bovis, 0.5-1.5 g of dried body of scorpion, 0.8-1.2 g of Notoginseng Radix Et Rhizoma, 0.05-0.15 g of cornu saigae tataricae powder, 1-4 g of ground beetle, 0.5-1.5 g of radix salviae miltiorrhizae and 0.8-1.6 g of lignum millettiae; the present invention related to a medicament is used for treating cardiovascular and cerebrovascular diseases and characterized by small volume, low dose, few adverse effect, and being easy to carry and take.

Patent: salvianolic acid composite for treating cardiovascular and cerebrovascular diseases and liver diseases, and application thereof, Patent No. CN200510094596.7, it is disclosed that: a composition composing of salvianolic acid and basic amino acid, or an alkaline glucose derivative, it has synergistic effects on the treatment of the cardiovascular and cerebrovascular diseases and the liver diseases; the alkaline amino acid is selected among arginine, lysine or histidine. The alkaline glucose derivative is selected from meglumine or glucosamine.

Patent: application of low molecular weight fucoidan in the preparation of medicaments for treating cardiovascular and cerebrovascular diseases, paten No. CN200610140395.0, it is disclosed that: the application of low molecular weight fucoidan in the preparation of medicaments treating cardiovascular and cerebrovascular diseases, especially the medicaments for treating ischemic cardiovascular and cerebrovascular diseases. The low molecular weight fucoidan in the present invention may be obtained through the degradation of fucoidan extracted from kelp, Ascophyllum nodosum, sea tangle, kelp or chorda, preferably through the degradation of the fucoidan oextracted from kelp, with a molecular weight of 8,000 to 100,000.

SUMMARY

The present invention provides a medicament for use in treating cardiovascular and cerebrovascular diseases in order to solve the deficiencies in the prior art for the purpose to achieve the following objectives hereof:

(1) the medicament can effectively reduce the content of triglyceride and total cholesterol in rats;

(2) the medicament can prolong mouse's survival time to 70 to 85 minutes during hypoxia;

(3) the medicament has a good therapeutic effect on arrhythmia induced by aconitine, and after administration of the medicament hereof, the incidence of ventricular tachycardia (VT) is 9/20-13/20, the incidence of ventricular fibrillation (VF) is 5/20-8/20, the recovery rate of sinus rhythm is 8/20-12/20, and the duration of ventricular premature beats (VP) is 2.24 to 3.59 min;

(4) the medicament has a good protective effect on rat myocardial ischemia induced by pituitrin.

In order to solve the above technical problems, the present invention adopts the following technical solution:

A medicament for use in treating cardiovascular and cerebrovascular diseases, wherein the medicament is a glycoprotein or a mixture polysaccharide and protein or a polypeptide or a protein; the glycoprotein comprises 1%-99% of sugar and 1%-99% of protein; and wherein the mixture of polysaccharide and protein comprises 1%-99% of sugar and 1%-99% of protein by weight. The glycoprotein has a molecular weight of 0.2-3000 kDa;

the following are further modifications to the above technical plan:

the medicament is a marine algal glycoprotein.

The marine algal glycoprotein comprises 1%-99% of sugar and 1%-99% of protein by weight; the mixture of marine algal polysaccharide and protein comprises 1%-99% of sugar—and 1%-99% of protein by weight.

The marine algal glycoprotein has a molecular weight of 0.2-3000 kDa;

as for the mixture of polysaccharide and the protein, the polysaccharide has a molecular weight of 0.2-3000 kDa and the protein has a molecular weight of 0.2-3000 kDa.

The medicament comprises 1-99 portions of glycoprotein and 1-25 portions of glucuronic acid by weight.

The medicament comprises 1-99 portions of marine algal glycoprotein and 1-26 portions of glucuronic acid by weight.

The medicament comprises 1-99 portions of marine algal glycoprotein, 1-26 portions of glucuronic acid and 2-13 portions of indigo naturalis by weight.

The algae comprises one or more kinds of blue-green algae, green algae, red algae, gold algae and brown algae.

The medicament comprises 1-99 portions of marine algal glycoprotein, 8-15 portions of indigo naturalis, and 7-14 portions of red bean and 1-15 portions of glucuronic acid by weight.

The medicament comprises 1-99 portions of marine algal glycoprotein, 8-15 portions of indigo naturalis, and 7-14 portions of red bean and 8-13 portions of hedyotic diffusa by weight.

The medicament comprises 1%-99% of sugar and 1%-99% of protein by weight.

The marine algal glycoprotein comprises 1%-99% of sugar and 1%-99% of protein-by weight.

Compared with the prior art, the advantages of the present invention are:

(1) The medicament hereof can effectively reduce the content of triglyceride and total cholesterol in rats; after four-week administration, the triglyceride value of the rat is decreased to 0.78-1.14 mmol/L, and the total cholesterol value can decrease to 1.97-2.64 mmol/L.

(2) The medicament hereof can prolong mouse's survival time to 70 to 85 minutes during hypoxia, survival time during hypoxia of the mice in the control group is only 46.23 minutes.

(3) The medicament has a good therapeutic effect on arrhythmia induced by aconitine, and after administration of the medicament, the incidence of ventricular tachycardia (VT) is 9/20-13/20, the incidence of ventricular fibrillation (VF) is 5/20-8/20, the recovery rate of sinus rhythm is 8/20-12/20, and the duration of ventricular premature beats (VP) is 2.24 to 3.59 min. In the model group, the incidence of ventricular tachycardia (VT) is 18/20, the incidence of ventricular fibrillation (VF) is 10/20, the recovery rate of sinus rhythm is 6/20, and the duration of ventricular premature beats (VP) is 1.22 min.

(4) The medicament has a good protective effect on rat myocardial ischemia induced by pituitrin, and the content of serum lactate dehydrogenase (LDH) is 8725.23-9200.23 U/L, the content of malondialdehyde (MDA) is 3.60-4.14 nmol/ml, and the content of superoxide dismutase (SOD) is 80.04-83.15 U/ml.

(5) The glycoprotein has the effects of improving microcirculation, dilating coronary arteries, improving myocardial blood supply, increasing the volume of blood flow of brain and coronary artery, slowing heart rate, reducing myocardial oxygen consumption index, improving blood myocardial metabolism, resisting thromboxane, increasing density lipoprotein, exerting anti-angiospasm effects, reducing platelet aggregation, and reducing the total cholesterol and triglyceride.

DETAILED DESCRIPTION OF THE EMBODIMENTS

The preferred embodiments of the present invention are described in the following, and the preferred embodiments described herein are only intended to illustrate and explain the invention, but not limited to this invention.

Embodiment 1

A Medicament for Use in Treating Cardiovascular and Cerebrovascular Diseases
  The medicament is a marine algal glycoprotein;
  the marine algal glycoprotein comprises 1% sugar (1%) and 99% protein by weight;
  the molecular weight is 0.2 kDa;
  the sugar is a polysaccharide;
  the marine algae is blue-green algae;
  the polysaccharide comprises: glucose, galactose, mannose and rhamnose;
  the protein comprises: arginine, lysine, serine, and threonine.

Embodiment 2

A Medicament for Use in Treating Cardiovascular and Cerebrovascular Diseases
  The medicament is a marine algal glycoprotein;
  the marine algal glycoprotein comprises, 5% sugar and 82% protein by weight;
  and the molecular weight is 15 kDa;
  the marine algae is green algae;
  the sugar is a polysaccharide;
  the polysaccharide comprises: glucose, galactose, mannose and rhamnose;
  the protein comprises: arginine, lysine, serine, and threonine.

Embodiment 3

A Medicament for Use in Treating Cardiovascular and Cerebrovascular Diseases
  The medicament is a marine algal glycoprotein;
  the marine algal glycoprotein comprises 10% sugar and 75% protein by weight;
  and the molecular weight is 5 kDa;
  the marine algae is blue-green algae;
  the sugar is a polysaccharide;
  the polysaccharide comprises: glucose, galactose, mannose and rhamnose;
  the protein comprises: arginine, lysine, serine, and threonine.

Embodiment 4

A Medicament for Use in Treating Cardiovascular and Cerebrovascular Diseases
  The medicament is a marine algal glycoprotein;
  the marine algal glycoprotein comprises 25% sugar and 70% protein by weight;
  and the molecular weight is 100 kDa;
  the marine algae is red algae;
  the sugar is a polysaccharide;
  the polysaccharide comprises: glucose, galactose, mannose and rhamnose;
  the protein comprises: arginine, lysine, serine, and threonine.

Embodiment 5

A Medicament for Use in Treating Cardiovascular and Cerebrovascular Diseases
  The medicament is a marine algal glycoprotein;
  The marine algal glycoprotein comprises 41% sugar and 59% protein by weight;
  and the molecular weight is 500 kDa;
  the marine algae is brown algae;
  the sugar is a polysaccharide;

the polysaccharide comprises: glucose, galactose, mannose and rhamnose;

the protein comprises: arginine, lysine, serine, and threonine.

Embodiment 6

A Medicament for Use in Treating Cardiovascular and Cerebrovascular Diseases
the medicament is a marine algal glycoprotein;
the marine algal glycoprotein comprises 99% sugar and 1% protein by weight;
the molecular weight is 3000 kDa;
the marine algae is gold algae;
the sugar is a polysaccharide;
the polysaccharide comprises: glucose, galactose, mannose and rhamnose;
the protein comprises: arginine, lysine, serine, and threonine.
the glycoprotein said in these above embodiments 1-6 further includes a pigment; the pigment is a natural pigment contained in the algal substances.

The above embodiments 1-6 could be summarized as:
A Medicament for Use in Treating Cardiovascular and Cerebrovascular Diseases
The medicament is a glycoprotein;
The glycoprotein comprises 1%-99% of sugar and 1%-99% of protein by weight;
the molecular weight is 0.2-30000 kDa;
the sugar is a polysaccharide;
the medicament includes synthetic glycoproteins and synthetic polysaccharides and proteins.
The protein comprises 20 kinds of amino acids and 8 kinds of synthetic amino acids;
the preparation method of the medicament: the glycoprotein is prepared into capsules and tablets etc. according to a conventional process; the mixture of the polysaccharide and the protein is prepared into capsules and tablets etc. according to a conventional process.

Embodiment 7

Application of the Medicament in Treating Cardiovascular and Cerebrovascular Diseases
(1) Effect of the Medicament Hereof on Blood Lipids in a Rat Model
   Experimental animal: SD rats, weighing 160-170 g;
   high fat diet formula: composed of 0.5%-2% cholesterol, 5% to 10% lard, 0.1% bile salt, 15% sucrose, 8% cooked soybean mea, 3% whole milk powde, and the remaining is comprised by basic feed.
   Experimental Method:
   Mice were randomly divided into 8 groups after entering the laboratory, namely normal control group, model control group, and present invention groups 1-6, 10 rats in each group, weighed and numbered;
   the animals in normal control group were fed with basic feeds, the mice in the model control group and the present invention groups were fed with high fat diets, and the experimental period was 4 weeks. During the experiment, the content of triglyceride and cholesterol was measured weekly; 4 weeks thereafter, the animals in the normal control group and the model control group were intragastrically administered distilled water, and those in the present invention groups 1-6, was administered the medicament said herein at a dose of 3 g/day, intragastrically, 3 times a day for 3 consecutive days, and at fourth week 4-after the initiation of the administration, the contents of glycerine and total cholesterol were detected; the experimental results are shown in Table 1.

TABLE 1

Effect of the medicament hereof on blood lipids in a rat model

| Group | Dose (g/day) | Triglyceride (mmol/L) | Total cholesterol (mmol/L) |
|---|---|---|---|
| Normal control group | — | 1.08 ± 0.17 | 1.88 ± 0.12 |
| Model control group | — | 1.94 ± 0.19 | 3.42 ± 0.15 |
| Embodiment 1 | 3 | 1.07 ± 0.12 | 2.46 ± 0.14 |
| Embodiment 2 | 3 | 0.86 ± 0.17 | 2.20 ± 0.11 |
| Embodiment 3 | 3 | 0.78 ± 0.14 | 1.97 ± 0.16 |
| Embodiment 4 | 3 | 0.90 ± 0.1 | 2.25 ± 0.15 |
| Embodiment 5 | 3 | 0.93 ± 0.13 | 2.37 ± 0.21 |
| Embodiment 6 | 3 | 1.14 ± 0.21 | 2.64 ± 0.23 |

In embodiments 1-6, The medicament hereof can effectively reduce the content of triglyceride and total cholesterol in rats at the dose of 3 g per day for three consecutive times; after four-week administration, the content of triglyceride in rats can decrease to 0.78-1.14 mmol/L, and that in total cholesterol can decrease to 1.97-2.64 mmol/L. Embodiments 2 and 3 are preferred embodiments.

TABLE 2

Effects of glycoprotein at different doses on blood lipids in a rat model

| Group | Dose (g/day) | Triglyceride (mmol/L) | Total cholesterol (mmol/L) |
|---|---|---|---|
| Normal control group | — | 1.08 ± 0.17 | 1.88 ± 0.12 |
| Model control group | — | 1.94 ± 0.19 | 3.42 ± 0.15 |
| Embodiment 2 | 1.5 | 0.99 ± 0.21 | 2.37 ± 0.13 |
| Embodiment 2 | 2 | 0.96 ± 0.17 | 2.29 ± 0.11 |
| Embodiment 2 | 3 | 0.86 ± 0.17 | 2.20 ± 0.11 |
| Embodiment 2 | 6 | 0.98 ± 0.1 | 2.25 ± 0.15 |
| Embodiment 2 | 12 | 1.04 ± 0.14 | 2.30 ± 0.11 |

(2) Effects on Mice's Survival Time During Hypoxia:
   70 mice were randomly divided into 7 groups, 10 in each group, and the control group: 10 ml/kg physiological saline; present invention groups 1-6 (corresponding to embodiments 1-6): The animals were administered the drugs said in embodiments 1-6 at a dose of 3 g/day, three times a day; 30 minutes thereafter, the mice were placed in a 500 ml grinding mouth bottle (containing 3 g of soda lime), then vaseline was applied and it was covered. The mice's death time was observed, and the effects on the survival time during hypoxia of normal mice are shown in Table 3.

TABLE 3

| Group | Survival time (minutes) |
|---|---|
| Control group | 46.23 ± 11.57 |
| Embodiment 1 | 75 ± 11.26 |
| Embodiment 2 | 80 ± 11.27 |
| Embodiment 3 | 85 ± 14.56 |
| Embodiment 4 | 77 ± 13.12 |
| Embodiment 5 | 75 ± 10.89 |
| Embodiment 6 | 70 ± 12.45 |

The glycoprotein of embodiments 1-6 can prolong mouse's survival time to 70-85 minutes and the survival time in the control group is only 46.23 minutes.

(3) Effects of Aconitine-Induced Arrhythmia in Rats:

140 healthy female Wistar rats were randomly divided into 7 groups, 20 in each group. Model group: administered the normal saline of an equal volume; present invention groups 1-6: (corresponding to embodiments 1-6): administered the drugs said in embodiments 1-6 at a dose of 3 g/day, 3 times a day; 30 minutes thereafter, the animals were anesthetized with 20% urethane (5 mg/kg), and then the animals were fixed on the rat table, and connected with the BL-420 biological function test system to plot the electrocardiogram; after the rats' ECG manifestations were stabilized, the mice in the model group and those in the group received the intravenous injected of 0.04% aconitine 1 ml/kg (40 µg/kg) in the sublingual vein, and the injection was completed within 5 s. The duration of the ventricular premature beats (VP) was observed. The incidence rate of ventricular tachycardia (VT) and the ventricular fibrillation (VF) and the recovery rate of sinus rhythm were recorded. The results of effects of aconitine-induced arrhythmia in rats are shown in Table 4.

TABLE 4

| | Arrhythmia (number of animals) | | | |
|---|---|---|---|---|
| Group | VT | VF | Recovery of sinus rhythm | Occurrence time of VP (min) |
| Model group | 18/20 | 10/20 | 6/20 | 1.22 ± 0.54 |
| Embodiment 1 | 12/20 | 8/20 | 8/20 | 2.90 ± 0.79 |
| Embodiment 2 | 10/20 | 6/20 | 10/20 | 3.08 ± 0.58 |
| Embodiment 3 | 9/20 | 5/20 | 12/20 | 3.59 ± 0.54 |
| Embodiment 4 | 11/20 | 7/20 | 10/20 | 3.27 ± 0.74 |
| Embodiment 5 | 11/20 | 7/20 | 9/20 | 3.21 ± 0.69 |
| Embodiment 6 | 13/20 | 8/20 | 8/20 | 2.24 ± 0.82 |

The medicaments of embodiments 1-6 have a good therapeutic effect on arrhythmia induced by aconitine, and after administration of the drug hereof, the incidence of ventricular tachycardia (VT) is 9/20-13/20, the incidence of ventricular fibrillation (VF) is 5/20-8/20, the recovery rate of sinus rhythm is 8/20-12/20, and the duration of ventricular premature beats (VP) is 2.24 to 3.59 min. In the model group, the incidence of ventricular tachycardia (VT) is 18/20, the incidence of ventricular fibrillation (VF) is 10/20, the recovery rate of sinus rhythm is 6/20, and the duration of ventricular premature beats (VP) is 1.22 min.

Embodiments 2 and 3 are preferred embodiments.

(4) Protective Effect of Pituitrin-Induced Myocardial Ischemia in Rats 80 healthy Wistar rats were randomly divided into 8 groups: normal control group: administered the normal saline of an equal volume. (2) Model group: administered the normal saline of an equal volume; present invention groups 1-6: (corresponding to embodiments 1-6): administered the medicaments of embodiments 1-6 at a dose of 3 g/day, 3 times a day.

Rats were subject to a screening test for the sensitivity of pituitrin on the day before the experiment. The method was as follows: the rats received the sublingual injection of pituitrin 1 U/kg, the changes in electrocardiogram were observed, and the pituitrin-sensitive rats were selected as the experimental animals (obvious elevation in T wave, and ST segment elevation by 0.1 mV). Sensitive rats obtained by screening were used in the model group and the mistletoe group, and the experiment was started 24 hours thereafter.

Normal control group: administered the normal saline of an equal volume. (2) Model group: administered the normal saline of an equal volume; present invention groups 1-6: (corresponding to embodiments 1-6): administered the medicaments of embodiments 1-6 at a dose of 3 g/day, 3 times a day. 60 minutes thereafter, the animals were anesthetized with 20% urethane (5 mg/kg), and then the animals were fixed on the rat table, and connected with the BL-420 biological function test system to plot the electrocardiogram. In the normal control group, the animals received the sublingual injection of normal saline, and those in the remaining groups received the intravenous injection of pituitrin at 1 U/kg. Thereafter, the changes in electrocardiogram were observed immediately and 1 min thereafter. The T wave and ST segment changes were used as indicators to determine the degree of myocardial ischemia and medicament effects. 60 min thereafter, blood was taken from the abdominal aorta, and serum was separated by centrifugation. Serum lactate dehydrogenase (LDH), superoxide dismutase (SOD) and malondialdehyde (MDA) levels were measured, and the results of the effects on LDH, MDA and SOD of rats with myocardial ischemia are shown in Table 5.

TABLE 5

| Group | LDH (U/L) | MDA (nmol/ml) | SOD (U/ml) |
|---|---|---|---|
| Normal control group | 7503.45 ± 1345.58 | 2.74 ± 0.67 | 96.58 ± 9.78 |
| Model group | 11825.47 ± 1218.41 | 4.97 ± 0.86 | 72.15 ± 8.97 |
| Embodiment 1 | 9150.57 ± 1147.56 | 4.05 ± 0.94 | 80.04 ± 9.54 |
| Embodiment 2 | 8826.13 ± 1245.07 | 3.69 ± 0.72 | 82.45 ± 8.53 |
| Embodiment 3 | 8725.23 ± 1319.73 | 3.60 ± 0.68 | 83.15 ± 8.67 |
| Embodiment 4 | 9000.14 ± 1348.06 | 3.85 ± 1.10 | 81.64 ± 9.43 |
| Embodiment 5 | 9100.49 ± 1254.16 | 3.97 ± 0.73 | 81.56 ± 8.15 |
| Embodiment 6 | 9200.23 ± 1378.58 | 4.14 ± 0.79 | 80.79 ± 8.59 |

The medicaments in embodiments 1-6 have a good protective effect on rat myocardial ischemia induced by pituitrin, and the content of serum lactate dehydrogenase (LDH) is 8725.23-9200.23 U/L, the content of malondialdehyde (MDA) is 3.60-4.14 nmol/ml, and the content of superoxide dismutase (SOD) is 80.04-83.15 U/ml. Embodiments 2 and 3 are preferred embodiments.

Embodiment 8

A Medicament for Use in Treating Cardiovascular and Cerebrovascular Diseases

It comprises 1 portion of marine algal glycoprotein and 1 portion of glucuronic acid by weight.

The marine algal glycoprotein comprises 5% sugar and 82% protein by weight;
 the molecular weight is 8 kDa;
 the marine algae is blue-green algae;
 the sugar is a polysaccharide;
 the polysaccharide comprises: glucose, galactose, mannose and rhamnose;
 the protein comprises: arginine, lysine, serine, and threonine.

Embodiment 9

A Medicament for Use in Treating Cardiovascular and Cerebrovascular Diseases

Like Embodiment 8, only the ratio of marine algal glycoprotein to glucuronic acid is changed as follows:
 it comprises 29 portions of marine algal glycoprotein and 7 portions of glucuronic acid by weight.

Embodiment 10

A Medicament for Use in Treating Cardiovascular and Cerebrovascular Diseases

Like Embodiment 8, only the ratio of marine algal glycoprotein to glucuronic acid is changed as follows:

it comprises 55 portions of marine algal glycoprotein and 16 portions of glucuronic acid by weight.

Embodiment 11

A Medicament for Use in Treating Cardiovascular and Cerebrovascular Diseases

Like Embodiment 8, only the ratio of marine algal glycoprotein to glucuronic acid is changed as follows:

it comprises 99 portions of marine algal glycoprotein and 26 portions of glucuronic acid by weight.

Embodiment 12

A Medicament for Use in Treating Cardiovascular and Cerebrovascular Diseases

It comprises 1 portion of marine algal glycoprotein, 1 portion of glucuronic acid and 2 portions of indigo naturalis by weight.

The marine algal glycoprotein comprises 10% sugar and 75% protein by weight;

and the molecular weight is 20 kDa;

the marine algae is *spirulina*;

the sugar is a polysaccharide;

the polysaccharide comprises: glucose, galactose, mannose and rhamnose;

the protein comprises: arginine, lysine, serine, and threonine.

Embodiment 13

A Medicament for Use in Treating Cardiovascular and Cerebrovascular Diseases

Like Embodiment 12, only the ratio of marine algal glycoprotein, glucuronic acid and indigo naturalis is changed as follows:

it comprises 29 portions of marine algal glycoprotein, 8 portions of glucuronic acid and 5 portions of indigo naturalis by weight.

Embodiment 14

A Medicament for Use in Treating Cardiovascular and Cerebrovascular Diseases

Like Embodiment 12, only the ratio of marine algal glycoprotein, glucuronic acid and indigo naturalis is changed as follows:

it comprises 60 portions of marine algal glycoprotein, 18 portions of glucuronic acid and 9 portions of indigo naturalis by weight.

Embodiment 15

A Medicament for Use in Treating Cardiovascular and Cerebrovascular Diseases

Like Embodiment 12, only the ratio of marine algal glycoprotein, glucuronic acid and indigo naturalis is changed as follows:

it comprises 99 portions of marine algal glycoprotein, 26 portions of glucuronic acid and 13 portions of indigo naturalis by weight.

Application of the Medicaments in Embodiment 8-Embodiment 15 in Treating Cardiovascular and Cerebrovascular Diseases:

Using the test method in Embodiment 7, the medicaments in Embodiment 8-Embodiment 15 in this invention group have the following application effects:

TABLE 6

Effects of the medicament hereof on blood lipids in a rat model

| Group | Dose (g/day) | Triglyceride (mmol/L) | Total cholesterol (mmol/L) |
|---|---|---|---|
| Normal control group | — | 1.08 ± 0.17 | 1.88 ± 0.12 |
| Model control group | — | 1.94 ± 0.19 | 3.42 ± 0.15 |
| Embodiment 8 | 3 | 0.80 ± 0.15 | 2.00 ± 0.15 |
| Embodiment 9 | 3 | 0.78 ± 0.12 | 1.97 ± 0.13 |
| Embodiment 10 | 3 | 0.60 ± 0.12 | 1.65 ± 0.12 |
| Embodiment 11 | 3 | 0.79 ± 0.15 | 1.96 ± 0.13 |
| Embodiment 12 | 3 | 0.75 ± 0.14 | 1.95 ± 0.12 |
| Embodiment 13 | 3 | 0.74 ± 0.15 | 1.94 ± 0.14 |
| Embodiment 14 | 3 | 0.62 ± 0.12 | 1.67 ± 0.12 |
| Embodiment 15 | 3 | 0.76 ± 0.16 | 1.93 ± 0.11 |

TABLE 7

Effects of the medicament hereof on mouse's survival time during hypoxia

| Group | Survival time (minutes) |
|---|---|
| Control Group | 46.23 ± 11.57 |
| Embodiment 8 | 85 ± 11.26 |
| Embodiment 9 | 87 ± 12.27 |
| Embodiment 10 | 108 ± 13.56 |
| Embodiment 11 | 88 ± 12.12 |
| Embodiment 12 | 88 ± 11.89 |
| Embodiment 13 | 90 ± 12.41 |
| Embodiment 14 | 105 ± 12.25 |
| Embodiment 15 | 92 ± 12.30 |

TABLE 8

Effects of the medicament hereof on aconitine-induced arrhythmia in rats

| Group | Arrhythmia (number of animals) | | Recovery of sinus rhythm | Occurrence time of VP (min) |
|---|---|---|---|---|
| | VT | VF | | |
| Model Group | 18/20 | 10/20 | 6/20 | 1.22 ± 0.52 |
| Embodiment 8 | 9/20 | 6/20 | 12/20 | 3.62 ± 0.57 |
| Embodiment 9 | 8/20 | 5/20 | 13/20 | 3.65 ± 0.59 |
| Embodiment 10 | 5/20 | 2/20 | 16/20 | 4.96 ± 0.55 |
| Embodiment 11 | 10/20 | 6/20 | 12/20 | 3.59 ± 0.57 |
| Embodiment 12 | 9/20 | 5/20 | 11/20 | 3.56 ± 0.51 |
| Embodiment 13 | 9/20 | 6/20 | 13/20 | 3.53 ± 0.50 |
| Embodiment 14 | 4/20 | 2/20 | 17/20 | 5.09 ± 0.56 |
| Embodiment 15 | 8/20 | 5/20 | 12/20 | 3.63 ± 0.53 |

TABLE 9

Protective effect of the medicament hereof on rat myocardial ischemia induced by pituitrin

| Group | LDH (U/L) | MDA (nmol/ml) | SOD (U/ml) |
|---|---|---|---|
| Normal control group | 7503.45 ± 1345.58 | 2.74 ± 0.67 | 96.58 ± 9.78 |
| Model Group | 11825.47 ± 1218.41 | 4.97 ± 0.86 | 72.15 ± 8.97 |
| Embodiment 8 | 8850.57 ± 1142.56 | 3.55 ± 0.94 | 82.04 ± 9.54 |
| Embodiment 9 | 8726.13 ± 1235.07 | 3.49 ± 0.72 | 82.45 ± 8.53 |
| Embodiment 10 | 7900.23 ± 1359.73 | 3.20 ± 0.68 | 90.15 ± 8.67 |

TABLE 9-continued

Protective effect of the medicament hereof on rat myocardial ischemia induced by pituitrin

| Group | LDH (U/L) | MDA (nmol/ml) | SOD (U/ml) |
|---|---|---|---|
| Embodiment 11 | 8800.14 ± 1318.06 | 3.58 ± 1.10 | 82.64 ± 9.43 |
| Embodiment 12 | 9100.49 ± 1204.16 | 3.67 ± 0.73 | 82.56 ± 8.15 |
| Embodiment 13 | 8920.23 ± 1332.28 | 3.80 ± 0.71 | 80.29 ± 8.35 |
| Embodiment 14 | 7800.23 ± 1352.57 | 3.14 ± 0.70 | 90.79 ± 8.29 |
| Embodiment 15 | 9100.23 ± 1348.58 | 3.74 ± 0.75 | 80.72 ± 8.31 |

In Embodiments 8-12, by changing the ratio of marine algal glycoprotein and glucuronic acid, the experiment found that Embodiment 10 was a preferred embodiment. In Embodiment 13-Embodiment 15, by changing the ratio of marine algal glycoprotein, glucuronic acid and indigo naturalis, the experiment found that, Embodiment 14 was a preferred embodiment.

Embodiment 16

A Medicament for Use in Treating Cardiovascular and Cerebrovascular Diseases

It comprises 1 portion of marine algal glycoprotein, 8 portions of indigo naturalis, 7 portions of red bean, and 1 portion of glucuronic acid by weight.

The marine algal glycoprotein comprises 25% sugar and 70% protein by weight;
the molecular weight is 8 kDa;
the marine algae is *Bangia atropurpurea* (Roth) C. Agardh;
the sugar is a polysaccharide;
the polysaccharide comprises: glucose, galactose, mannose and rhamnose;
the protein comprises: arginine, lysine, serine, and threonine.

Embodiment 17

A Medicament for Use in Treating Cardiovascular and Cerebrovascular Diseases

It comprises 45 portions of marine algal glycoprotein, 11 portions of indigo naturalis, 9 portions of red bean, and 7 portions of glucuronic acid by weight.

The marine algal glycoprotein comprises 25% sugar and 70% protein by weight;
and the molecular weight is 12 kDa;
the marine algae is *Bangia atropurpurea* (Roth) C. Agardh;
the sugar is a polysaccharide;
the polysaccharide comprises: glucose, galactose, mannose and rhamnose;
the protein comprises: arginine, lysine, serine, and threonine.

Embodiment 18

A Medicament for Use in Treating Cardiovascular and Cerebrovascular Diseases

It comprises 99 portions of marine algal glycoprotein, 15 portions of indigo naturalis, 14 portions of red bean, and 15 portions of glucuronic acid by weight.

The marine algal glycoprotein comprises 25% sugar and 70% protein by weight;
and the molecular weight is 60 kDa;
the marine algae is *Bangia atropurpurea* (Roth) C. Agardh;
the sugar is a polysaccharide;
the polysaccharide comprises: glucose, galactose, mannose and rhamnose;
the protein comprises: arginine, lysine, serine, and threonine.

Embodiment 19

A Medicament for Use in Treating Cardiovascular and Cerebrovascular Diseases

It comprises 1 portion of marine algal glycoprotein, 8 portions of indigo naturalis, 7 portions of red bean, and 8 portions of hedyotic diffusa by weight.

The marine algal glycoprotein comprises 41% sugar and 59% protein by weight;
the molecular weight is 8 kDa;
the marine algae is gulfweed;
the sugar is a polysaccharide;
the polysaccharide comprises: glucose, galactose, mannose and rhamnose;
the protein comprises: arginine, lysine, serine, and threonine.

Embodiment 20

A Medicament for Use in Treating Cardiovascular and Cerebrovascular Diseases

It comprises 39 portions of marine algal glycoprotein, 12 portions of indigo naturalis, 11 portions of red bean, and 10 portions of hedyotic diffusa by weight.

The marine algal glycoprotein comprises 41% sugar and 59% protein by weight;
and the molecular weight is 20 kDa;
the marine algae is blue-green algae;
the sugar is a polysaccharide;
the polysaccharide comprises: glucose, galactose, mannose and rhamnose;
the protein comprises: arginine, lysine, serine, and threonine.

Embodiment 21

A Medicament for Use in Treating Cardiovascular and Cerebrovascular Diseases

It comprises 99 portions of marine algal glycoprotein, 15 portions of indigo naturalis, 14 portions of red bean, and 13 portions of hedyotic diffusa by weight.

The marine algal glycoprotein comprises sugar (41%) and protein (59%) by weight;
and the molecular weight is 200 kDa;
the marine algae is blue-green algae;
the sugar is a polysaccharide;
the polysaccharide comprises: glucose, galactose, mannose and rhamnose;
the protein comprises: arginine, lysine, serine, and threonine.

Application of the Medicaments in Embodiment 16-Embodiment 21 in Treating Cardiovascular and Cerebrovascular Diseases:

Using the test method said in Embodiment 7, the medicaments said in Embodiment 16-Embodiment 21 in this invention group have the following application effects:

TABLE 10

Effects of the medicament hereof on blood lipids in a rat model

| Group | Dose (g/day) | Triglyceride (mmol/L) | Total cholesterol (mmol/L) |
|---|---|---|---|
| Normal control group | — | 1.08 ± 0.17 | 1.88 ± 0.12 |
| Model control group | — | 1.94 ± 0.19 | 3.42 ± 0.15 |
| Embodiment 16 | 3 | 0.78 ± 0.15 | 1.89 ± 0.15 |
| Embodiment 17 | 3 | 0.32 ± 0.12 | 1.35 ± 0.13 |
| Embodiment 18 | 3 | 0.70 ± 0.12 | 1.87 ± 0.12 |
| Embodiment 19 | 3 | 0.75 ± 0.15 | 1.86 ± 0.13 |
| Embodiment 20 | 3 | 0.35 ± 0.14 | 1.30 ± 0.12 |
| Embodiment 21 | 3 | 0.73 ± 0.15 | 1.85 ± 0.14 |

TABLE 11

Effects of the medicament hereof on mouse's survival time during hypoxia

| Group | Survival time (minutes) |
|---|---|
| Control group | 46.23 ± 11.57 |
| Embodiment 16 | 90 ± 11.76 |
| Embodiment 17 | 120 ± 12.17 |
| Embodiment 18 | 91 ± 13.46 |
| Embodiment 19 | 92 ± 12.32 |
| Embodiment 20 | 119 ± 11.99 |
| Embodiment 21 | 91 ± 12.11 |

TABLE 12

Effects of the medicament hereof on aconitine-induced arrhythmia in rats

| Group | Arrhythmia (number of animals) VT | VF | Recovery of sinus rhythm | Occurrence time of VP (min) |
|---|---|---|---|---|
| Model Group | 18/20 | 10/20 | 6/20 | 1.22 ± 0.52 |
| Embodiment 16 | 8/20 | 6/20 | 11/20 | 3.68 ± 0.47 |
| Embodiment 17 | 2/20 | 1/20 | 18/20 | 5.65 ± 0.49 |
| Embodiment 18 | 6/20 | 5/20 | 12/20 | 3.96 ± 0.45 |
| Embodiment 19 | 7/20 | 6/20 | 12/20 | 3.90 ± 0.47 |
| Embodiment 20 | 1/20 | 0/20 | 19/20 | 5.56 ± 0.41 |
| Embodiment 21 | 6/20 | 5/20 | 13/20 | 3.63 ± 0.40 |

TABLE 13

Protective effect of the medicament hereof on rat myocardial ischemia induced by pituitrin

| Group | LDH (U/L) | MDA (nmol/ml) | SOD (U/ml) |
|---|---|---|---|
| Normal control group | 7503.45 ± 1345.58 | 2.74 ± 0.67 | 96.58 ± 9.78 |
| Model Group | 11825.47 ± 1218.41 | 4.97 ± 0.86 | 72.15 ± 8.97 |
| Embodiment 16 | 8650.57 ± 1142.56 | 3.50 ± 0.94 | 84.04 ± 9.54 |
| Embodiment 17 | 7500.13 ± 1230.07 | 2.78 ± 0.72 | 96.45 ± 8.23 |
| Embodiment 18 | 8550.23 ± 1309.73 | 3.30 ± 0.68 | 84.15 ± 8.27 |
| Embodiment 19 | 8700.14 ± 1328.06 | 3.48 ± 0.80 | 82.64 ± 9.03 |
| Embodiment 20 | 7400.49 ± 1284.16 | 2.76 ± 0.63 | 96.56 ± 8.35 |
| Embodiment 21 | 8820.23 ± 1302.28 | 3.60 ± 0.61 | 82.29 ± 8.31 |

In Embodiments 16-18, by changing the ratio of marine algal glycoprotein, indigo naturalis and glucuronic acid, the experiment found that, Embodiment 17 was a preferred embodiment.

In Embodiments 19-21, by changing the ratio of marine algal glycoprotein, indigo naturalis and hedyotic diffusa, the experiment found that, Embodiment 20 was a preferred embodiment.

Embodiment 22

A Medicament for Use in Treating Cardiovascular and Cerebrovascular Diseases

It comprises by weight, the following components:

70 portions of marine algal glycoprotein, 5 portions of sappan wood, 7 portions of Sparganii Rhizoma, 6 portions of semen cassia, 5 portions of Lamiophlomis rotata Kudo- and 10 portions of herba lobeliae chinensis.

The glycoprotein is a marine algal glycoprotein;

the marine algal glycoprotein comprises 7% sugar and 80% protein by weight;

the molecular weight is 8 kDa;

the marine algae is synuraceae urelin.

Embodiment 23

A Medicament for Use in Treating Cardiovascular and Cerebrovascular Diseases

It comprises by weight, the following components:

80 portions of marine algae glycoprotein, 6 portions of bezoar, 9 portions of princesplume ladysthumb fruit, 5 portions of alismatis rhizoma, 4 portions of corydalis tuber, and 6 portions of *hibiscus rosa-sinensis;* the glycoprotein is a marine algal glycoprotein;

the marine algal glycoprotein comprises 14% sugar and 72% protein by weight;

and the molecular weight is 22 kDa;

the marine algae is *Platymonas.*

Embodiment 24

A Medicament for Use in Treating Cardiovascular and Cerebrovascular Diseases

It comprises by weight, the following components:

85 portions of marine algae glycoprotein, 11 portions of red peony root, 5 portions of mylabris, 6 portions of fleece-flower root, 8 portions of rabdosia rubesens, and 6 portions of Japanese thistle;

the glycoprotein is a marine algal glycoprotein;

the marine algal glycoprotein comprises 18% sugar and 62% protein by weight;

and the molecular weight is 30 kDa;

the marine algae is nostocales.

Embodiment 25

A Medicament for Use in Treating Cardiovascular and Cerebrovascular Diseases

It comprises by weight, the following components:

70 portions of marine algae glycoprotein, 6 portions of green tea, 5 portions of zedoary, 3 portions of cattail pollen, 4 portions of herba polygalae *Japonica* and 8 portions of *dianthi* herba;

the glycoprotein is a marine algal glycoprotein;

the marine algal glycoprotein comprises 30% sugar and 55% protein by weight;

and the molecular weight is 40 kDa;

the marine algae is *Anabena.*

Embodiment 26

Preparation Method of a Medicament for Use in Treating Cardiovascular and Cerebrovascular Diseases Step 1: Weighing Weigh the marine algae glycoprotein and all Chinese medicine components according to the formula;

Step 2: Extraction of Chinese Medicine
(1) Washing
Wash all Chinese medicine components with clear water, and remove the impurities;
(2) Crash and Microwave Extraction The Chinese medicine is pulverized into 100-mesh medicinal material powder, 10 times of 50% ethanol is added, the temperature is controlled at 60° C., microwave radiation is performed at the microwave irradiation of 260 W, microwave wavelength of 130 mm, a frequency of 1200 MHz for 5 min, then filtration is carried out, and finally the filtrate is collected;

the medicine dregs are separated, 12 times of clear water is added, the temperature is controlled at 50° C., microwave radiation is performed at the microwave irradiation of 200 W, microwave wavelength of 1430 mm, a frequency of 1250 MHz for 5 min, then filtration is carried out, and finally the filtrate is collected;

pool the filtrate collected from the two procedures; atomize and dry to prepare them into Chinese medicine powder;

after the aforementioned atomization and drying, pool the above filtrates collected from the two procedures; filter them through a 0.45 μm microporous membrane to obtain the subsequent filtrate, and the obtained subsequent filtrate is introduced into a dual-flow spiral nozzle of a Büchi290 small-sized spray dryer through a peristaltic pump, and the inlet temperature is controlled to 125. ° C., the feeding rate to 3 mL/min, and atomize and dry them.

Step 3 Add Marine Algae Glycoprotein

Mixing the powder of marine algae glycoprotein with the above Chinese medicine powder evenly; prepare them into the medicaments of different dosage forms such as capsules and tablets.

Application of the Medicaments in Embodiment 22-Embodiment 25 in Treating Cardiovascular and Cerebrovascular Diseases:

Applying the test method specified in Embodiment 7, this invention group is the medicaments mentioned in Embodiment 22-Embodiment 25, the applicable effects are as follows:

TABLE 14

Effects of the medicament in the present invention on blood lipids in a rat model

| Group | Dose (g/day) | Triglyceride (mmol/L) | Total cholesterol (mmol/L) |
|---|---|---|---|
| Normal control group | — | 1.08 ± 0.17 | 1.88 ± 0.12 |
| Model control group | — | 1.94 ± 0.19 | 3.42 ± 0.15 |
| Embodiment 22 | 3 | 0.48 ± 0.15 | 1.65 ± 0.15 |
| Embodiment 23 | 3 | 0.42 ± 0.12 | 1.55 ± 0.13 |
| Embodiment 24 | 3 | 0.40 ± 0.12 | 1.47 ± 0.12 |
| Embodiment 25 | 3 | 0.45 ± 0.15 | 1.56 ± 0.13 |

TABLE 15

Effects of the medicament in the present invention on mouse's survival time during hypoxia

| Group | Survival time (minutes) |
|---|---|
| Control Group | 46.23 ± 11.57 |
| Embodiment 22 | 110 ± 11.76 |
| Embodiment 23 | 109 ± 12.17 |
| Embodiment 24 | 108 ± 13.46 |
| Embodiment 25 | 112 ± 12.32 |

TABLE 16

Effects of the medicament in the present invention on aconitine-induced arrhythmia in rats

| Group | Arrhythmia (number of animals) VT | Arrhythmia (number of animals) VF | Recovery of sinus rhythm | Occurrence time of VP (min) |
|---|---|---|---|---|
| Model Group | 18/20 | 10/20 | 6/20 | 1.22 ± 0.52 |
| Embodiment 22 | 4/20 | 3/20 | 13/20 | 4.68 ± 0.47 |
| Embodiment 23 | 3/20 | 1/20 | 15/20 | 5.25 ± 0.49 |
| Embodiment 24 | 2/20 | 2/20 | 13/20 | 4.96 ± 0.45 |
| Embodiment 25 | 3/20 | 3/20 | 16/20 | 4.90 ± 0.47 |

TABLE 17

Protective effect of the medicament in the present invention on rat myocardial ischemia induced by pituitrin

| Group | LDH (U/L) | MDA (nmol/ml) | SOD (U/ml) |
|---|---|---|---|
| Normal control group | 7503.45 ± 1345.58 | 2.74 ± 0.67 | 96.58 ± 9.78 |
| Model group | 11825.47 ± 1218.41 | 4.97 ± 0.86 | 72.15 ± 7.97 |
| Embodiment 22 | 7650.57 ± 1142.56 | 3.00 ± 0.94 | 94.04 ± 7.54 |
| Embodiment 23 | 7700.13 ± 1230.07 | 2.88 ± 0.72 | 93.45 ± 7.23 |
| Embodiment 24 | 7850.23 ± 1309.73 | 2.98 ± 0.68 | 94.15 ± 7.27 |
| Embodiment 25 | 8000.14 ± 1328.06 | 3.12 ± 0.80 | 92.64 ± 8.03 |

Embodiment 27

Effects of the Medicaments in the Present Invention in Breaking Blood Vessel Thrombi Clinical trials were carried on the medicaments in Embodiments 8-22 in the present invention at the dose of three times per day, 1 g per time and the results are shown in Table 18 and Table 19.

TABLE 18

| | | Whole blood viscosity | Fibrin mg % | AT-III % | Plasmiongen U | Prothrombin time (time s) |
|---|---|---|---|---|---|---|
| | Before administration | 5.28 | 479.12 | 104.5 | 6.99 | 12.15 |
| After administration | Embodiment 8 | 4.56 | 435.6 | 80.56 | 7.25 | 12.59 |
| | Embodiment 9 | 4.58 | 420.56 | 82.25 | 7.29 | 12.58 |
| | Embodiment 10 | 3.50 | 300.59 | 47.18 | 7.88 | 14.65 |
| | Embodiment 11 | 4.41 | 425.9 | 81.9 | 7.31 | 12.75 |
| | Embodiment 12 | 4.30 | 425.9 | 79.8 | 7.33 | 12.79 |

TABLE 18-continued

|  | Whole blood viscosity | Fibrin mg % | AT-III % | Plasmiongen U | Prothrombin time (time s) |
|---|---|---|---|---|---|
| Embodiment 13 | 4.42 | 415.26 | 76.53 | 7.37 | 12.86 |
| Embodiment 14 | 3.48 | 294.26 | 45.23 | 7.91 | 14.87 |
| Embodiment 15 | 4.35 | 412.4 | 77.5 | 7.36 | 12.89 |

TABLE 19

|  |  | Whole blood viscosity | Fibrin mg % | AT-III % | Plasmiongen U | Prothrombin time (time s) |
|---|---|---|---|---|---|---|
| Before administration | | 5.28 | 479.12 | 104.5 | 6.99 | 12.15 |
| After administration | Embodiment 16 | 4.42 | 430.6 | 80.36 | 7.28 | 12.69 |
| | Embodiment 17 | 3.45 | 301.16 | 46.25 | 8.12 | 14.98 |
| | Embodiment 18 | 4.52 | 432.5 | 81.4 | 7.30 | 12.51 |
| | Embodiment 19 | 4.30 | 427.9 | 80.4 | 7.45 | 12.78 |
| | Embodiment 20 | 3.34 | 316.5 | 44.8 | 8.26 | 14.63 |
| | Embodiment 21 | 4.45 | 428.26 | 84.23 | 7.39 | 12.66 |
| | Embodiment 22 | 3.30 | 310.5 | 41.4 | 8.35 | 14.77 |
| | Embodiment 23 | 3.31 | 302.5 | 42.5 | 8.30 | 14.69 |

For the medicaments mentioned in the present invention, have a pH is between 5.3 and 9.8, and 6.5-7.5 is preferred.

The invention has been subjected to a large number of experiments, and we have carried out multiple tests using a mixture of marine shells, bones of livestock and poultry, a mixture of protides, polysaccharides and proteins extracted from the skeleton of marine animals, and the objectives of the invention have also been achieved.

Embodiment 28

A Medicament for Use in Treating Cardiovascular and Cerebrovascular Diseases

The medicament is a mixture of polysaccharides and proteins;

the medicament comprises 1%-99% of polysaccharide and 1%-99% of protein by weight;

the polysaccharide comprises: glucose, galactose, mannose and rhamnose;

the protein comprises: arginine, lysine, serine, and threonine.

As for the mixture of polysaccharide and the protein, the polysaccharide has a molecular weight of 0.2-3000 kDa and the protein has a molecular weight of 0.2-3000 kDa.

The mixture of polysaccharides and proteins, further a mixture of algal polysaccharides and algal proteins;

the mixture of the algal polysaccharide and the algal protein also comprises a pigment;

the pigment is a natural pigment contained in the algal substance;

the algal protein may be phycocyanin, phycoerythrin or algae xanthoprotein.

The glycoprotein includes synthetic glycoprotein, synthetic polysaccharide and protein.

The medicament hereof has a No Observed Adverse Effect Level (NOAEL) of 1.6 g/kg for 12-week oral administration for dogs, which is equivalent to 50 times the equivalent dose for humans, so it is concluded that the safety of the clinical trial can be guaranteed.

The medicine described in the present invention can also be a health care product or a food.

The basic principles and main features of the present invention and the advantages of the present invention are shown and described above. It should be understood by the technicians in this field that, the present invention is not limited by the foregoing embodiments, and that what are described in the aforementioned embodiments and instructions are only the principles of this invention; without departing from the spirit and scope of the invention, this invention may be subject to various changes and modifications, which will be included within the scope of the invention as claimed. The scope of the invention is defined by the appended claims and their equivalents.

What is claimed is:

1. A medicament for use in treating cardiovascular and cerebrovascular diseases, comprising: a marine algae glycoprotein, indigo naturalis, red bean, and glucuronic acid in a ratio of 45:11:9:7 by weight, wherein the marine algae glycoprotein comes from *Bangia atropurpurea* (Roth) C. Agardh and comprises 25% of sugar—and 70% of protein by weight with a molecular weight of 12 kDa.

* * * * *